US007686849B2

(12) United States Patent
Forbes et al.

(10) Patent No.: US 7,686,849 B2
(45) Date of Patent: Mar. 30, 2010

(54) OXIDATIVE HAIR DYES AND RELATED TOPICAL COMPOSITIONS

(75) Inventors: Neil Robert Forbes, Nottingham (GB); Edward Galley, Nottingham (GB); Christine Sheard, Nottingham (GB)

(73) Assignee: The Boots Company PLC., Nottingham (GB)

( * ) Notice: Subject to any disclaimer, the term of this patent is extended or adjusted under 35 U.S.C. 154(b) by 94 days.

(21) Appl. No.: 11/910,850

(22) PCT Filed: Apr. 6, 2006

(86) PCT No.: PCT/GB2006/050080

§ 371 (c)(1),
(2), (4) Date: Oct. 5, 2007

(87) PCT Pub. No.: WO2006/106366

PCT Pub. Date: Oct. 12, 2006

(65) Prior Publication Data

US 2008/0233068 A1    Sep. 25, 2008

(30) Foreign Application Priority Data

Apr. 6, 2005   (GB) ................... 0506930.7
Sep. 10, 2005  (GB) ................... 0518504.6

(51) Int. Cl.
*A61Q 5/10*  (2006.01)
(52) U.S. Cl. .............. 8/405; 8/406; 8/435; 8/626; 8/632; 132/202; 132/208
(58) Field of Classification Search .............. 8/405, 8/406, 435, 626, 632; 132/202, 208
See application file for complete search history.

(56) References Cited

U.S. PATENT DOCUMENTS

| 5,089,253 | A | * | 2/1992 | Halloran ................ 424/47 |
| 6,129,770 | A |   | 10/2000 | Deutz et al. |
| 6,352,699 | B1 |  | 3/2002 | Mondet et al. |
| 6,419,710 | B1 |  | 7/2002 | Demeulenaere et al. |
| 6,730,133 | B1 | * | 5/2004 | Plos et al. ................ 8/405 |
| 2004/0138436 | A1 | * | 7/2004 | Schacht et al. ........... 534/844 |

FOREIGN PATENT DOCUMENTS

| EP | 0 117 360 A1 | 9/1984 |
| GB |    756002 A  | 8/1956 |

OTHER PUBLICATIONS

STIC Search Report dated Dec. 5, 2008.*
Hagan et al., "Antiperspirant compositions based on titanium salts", International Journal of Cosmetic Science, 19, 271-280, 1997.
Database WPI, Section CH, Week 199030, Derwent Publications Ltd., XP002391038 & JP 02 153973 A (Kao Corp) Jun. 13, 1990.
John F. Corbett, "Hair Colorants: Chemistry and Toxicology", Cosmetic Science Monographs No. Two, 5 pgs.
"The Cosmetic Products (Safety) Regulations 2004", Statutory Instruments, 2004, No. 2152, Consumer Protection, 33 pgs.
The Cosmetic Products (Safety) Regulations 2008, Statutory Instruments, 2008, No. 1284, Consumer Protection, pp. 103-114.

* cited by examiner

*Primary Examiner*—Eisa B Elhilo
(74) *Attorney, Agent, or Firm*—Rothwell, Figg, Ernst & Manbeck, P.C.

(57) ABSTRACT

An oxidative hair dye system comprises a hair dye, an organometallic compound and an oxidising agent. The organometallic compound is preferably an organotitanate compound, particularly a tetraalkyl titanate or a titanate chelate. Such compounds are also useful for enhancing the substantivity of topical compositions applied to the body, which comprise one or more cosmetic and/or therapeutic benefit agents, a bonding agent having hydrolysable or exchangeable ligands, and a carrier.

23 Claims, No Drawings

OXIDATIVE HAIR DYES AND RELATED TOPICAL COMPOSITIONS

CROSS REFERENCE TO RELATED APPLICATION

This application is a 35 USC 371 National Phase Entry Application from PCT/GB2006/050080, filed Apr. 6, 2006, and designating the United States This invention relates to improved oxidative hair dye systems, and to methods of using such compositions to impart colour to the hair. The invention also relates to compositions for topical application to a variety of substrates, including the skin, hair, nails, lips and mucous membranes. These compositions comprise one or more bonding agents that have hydrolysable or exchangeable ligands and which are capable of attaching a cosmetic or therapeutic benefit agent to the substrate.

Hair colour is due to the presence of melanin pigments in the cortex of the hair shaft. There are two kinds of pigment: eomelanin, a dark pigment which predominates in black and brunette hair, and phaeomelanin, a lighter pigment which is found in red and blond hair. The cuticle is a smooth, colourless and translucent sheath that surrounds the cortex. The colour we see is due to a combination of light that has passed through the coloured cortex and light that is reflected by the cuticle.

For many years the colour of hair has been altered using natural and artificial substances. Modern hair colourants can be grouped broadly into six types, described as natural, progressive, temporary, semi-permanent, demi-permanent and permanent.

Natural hair colourants have been used since ancient times to alter the shade of hair. Henna is the most frequently used natural hair colourant. It is widely used to redden hair, especially dark hair, but the colour produced only lasts through several shampoos. Also, results can be somewhat unpredictable as the concentration is difficult to control.

Progressive hair colourants are composed of metallic salts (eg lead or bismuth) which oxidise to form dark coloured compounds on exposure to air.

Temporary hair colourants are acidic dyes which do not penetrate the hair shaft to any significant degree, and are generally washed off the hair after one or two washes. They affect the way in which the cuticle reflects light, and they tend to make hair look dull. Examples include dyes such as Ponceau Red and C.I. Acid Yellow.

Semi-permanent hair dyes, often known as direct dyes, are small molecules that can pass through the cuticle into the cortex easily and without damaging the scales of the cuticle. Whilst this affords more durability than temporary dyes, the dyes can also be washed out easily, and typically last for up to about 6-8 washes. Since no bleaching agents are used, it is not possible to lighten the hair using semi-permanent dyes. Examples of such dyes include HC Blue 2 and HC Orange 1.

Permanent hair dyes, also called oxidative hair dyes, are generally marketed as two-component kits. One component contains dye precursor molecules that are small enough to penetrate the hair shaft. The other component, which may be described as the developing lotion, contains an oxidising agent, eg hydrogen peroxide. The two components are mixed immediately before application to the hair. The precursor molecules and the oxidising agent diffuse into the hair shaft where the oxidising agent initiates a cascade of reactions, causing the dye molecules to combine to form coloured dimers, trimers and larger molecules. The increase in molecular size means that dyes become trapped under the hair cuticle, and will not wash out. In addition to initiating the polymerisation reaction, the oxidising agent bleaches the hair's natural melanin, and so lighter colours than the original colour can be achieved.

Another integral part of a permanent hair dye system is an alkaline material, usually ammonia, which is used to raise the hair cuticle allowing the dye precursor molecules to penetrate more easily. An alkaline pH is also necessary for the hydrogen peroxide to degrade to produce oxygen. Furthermore, varying the pH can vary the relative reaction rates of the polymerisation reactions between dye molecules, and hence influence the shade of the hair colour produced. The alkali is usually included in the composition containing the dye precursor molecules.

Colour formation is dependent on the precursors and direct dyes present, the pH, and the duration of contact of the hair dye composition with the hair. The colour achieved by a permanent hair colourant is relatively long lasting, although it does fade over time (typically noticeable by 20-24 washes), and so the timing of reapplication is usually governed by the desire to enhance the colour, as well as the emergence of new, uncoloured roots.

Demi-permanent colourants are very similar to permanent colourants, except that lower levels of hydrogen peroxide and no ammonia are used, meaning that the products are milder, but less durable. Typically, the colour lasts between 12 and 24 washes.

In the context of the present invention by "oxidative hair dye" is meant a demi-permanent or permanent dye system that includes an oxidising agent.

Semi-permanent, demi-permanent and permanent hair colourants are described in the USA as Level 1, 2 and 3 colourants respectively.

Permanent hair dyes can be used singly or, more commonly, in combination with other dyes (sometimes up to about 10). Dyes that will react with themselves to form colours are known as "bases" (or "primary intermediates"), the best known of which is p-phenylenediamine (PPD). Bases can be combined to produce different colours. There is another group of dyes that will combine with bases to form coloured molecules, but which cannot form colours in the absence of one or more bases. These dyes are called "couplers" (or "colour modifiers"). All conventional permanent hair dyes contain at least one base.

The following tables show some commonly used bases and couplers (J. F. Corbett, *Hair colorants: chemistry and toxicology*, H. Butler (ed). Weymouth: Micelle Press, 1998), though it should be noted that there are numerous other hair dyes not listed which are used less frequently.

| Base | Colour on hair |
| --- | --- |
| p-Phenylenediamine | Dark brown/black |
| 2,5-Diaminotoluene | Reddish brown |
| 2-Chloro-p-phenylenediamine | Dark grey-black |
| N-Phenyl-p-phenylenediamine | Dark grey/black |
| N,N-Bis(2-hydroxyethyl)-p-phenylenediamine | Brown |
| 3-Methyl-4-aminophenol | Brown |
| 2--Hydroxyethyl-p-phenylenediamine | Brown |
| p-Aminophenol | Light auburn |
| N-Methyl-p-aminophenol | Pale blond |

| Coupler | Colour on hair with base |
| --- | --- |
| Resorcinol | (A) greenish brown; (C) yellow-grey |
| 4-Chlororesorcinol | (A) greenish brown |
| 2-Methylresorcinol | (A) yellow brown; (C) grey-violet |
| 1-Naphthol | (A) purple; (B) blue |
| 2-Methyl-1-naphthol | (A) blue-violet, (C) red |
| 1,5-Dihydroxynaphthalene | (A) blue-grey |
| 1,7-Dihydroxynaphthalene | (A) violet |
| 5-Hydroxybenzodioxane | — |
| 2,5-Dihydroxy-4-methylpyridine | — |
| m-Aminophenol | (A) magenta/brown |
| 4-Amino-2-hydroxytoluene | (A) magenta; (C) orange-red |
| 5-(2-Hydroxyethyl)amino-2-methylphenol | (C) orange-red |
| 6-Hydroxybenzomorpholine | — |
| m-Phenylenediamine | (A) blue; (B) green-blue |
| 2,4-Diaminophenoxyethanol | (A) violet-blue; (C) dark red |
| 2,6-Diaminopyridine | (A) blue |
| 3,3'-Dihydroxydiphenylamine | — |
| o-Aminophenol | — |

(A) = p-Phenyldiamine
(B) = N,N-Bis(2-hydroxyethyl)-p-phenylenediamine
(C) = p-Aminophenol There are clear advantages of using an oxidative hair dye instead of a natural, progressive or semi-permanent hair dye, principally the length of time or the number of washes for which the hair is coloured. Hair colour may also be more consistent.

However, the use of oxidative hair dyes is also accompanied by a number of disadvantages. Oxidising agents can destroy the disulfide bonds in the hair keratin, and so regular use of an oxidative hair dye may eventually lead to the hair protein becoming so weak that the hair breaks.

The range of colours that can be produced by current oxidative hair dyes is limited by the number of base molecules available. In particular, permanent red shades are difficult to achieve using conventional oxidative dye combinations, and tend to wash out quickly.

Furthermore, it has been speculated that a number of permanent hair dyes are associated with health risks. Some are known allergens (where a number of common oxidation dyes are used, the phrase "can cause an allergic reaction" must be displayed on pack), and some have been linked with cancer, though the debate is ongoing. The dye of greatest concern on health grounds is PPD, and products containing this dye must display the statement "contains phenylene diamines". It is sometimes claimed that darker dyes, which are chemically similar to carcinogenic coal tars, are the least safe, but unfortunately it is difficult to produce dark permanent colours without the use of PPD. The use of PPD was previously banned in France and Germany, where an alternative base (2,5-diaminotoluene) was used instead, though the ban has since been lifted.

Permanent hair dyes use ammonia, and this must be stated on the product packaging. Ammonia has an unpleasant smell, and can also damage the hair. Raising the scales of the cuticle for penetration by the oxidising agent is in itself a potentially damaging process. Repeated use of permanent hair colourants can leave permanently raised scales and upset the moisture content of the hair, leaving it weak and brittle with little shine or lustre.

There thus exists a need for improved oxidative hair dye compositions that do not contain dye molecules which have safety or toxicological concerns associated with them. Oxidative hair dye compositions that avoid the use of ammonia or other harsh alkaline materials, and produce a colour that does not fade, would clearly present a significant advantage over the prior art.

In addition, there exists a need for oxidative hair dye compositions that produce a greater range of colours, in particular red colours.

Numerous types of cosmetic benefit agent can be applied to the skin, hair, lips or mucous membranes. These agents are applied for various purposes, eg as moisturisers, humectants, colour cosmetics, etc. A common problem, however, is the lack of substantivity of the cosmetic benefit agents to the surface to which they are applied, meaning that the long term wear properties and transfer resistance are not as good as might be wished by the user.

There therefore exists a need for cosmetic compositions that have improved substantivity, yet which incorporate agents that are safe and efficacious. The present invention seeks to provide such compositions.

Similarly, many therapeutic benefit agents are applied to the skin. Examples include antimicrobial agents, anti-acne agents, anti-fungal agents, anti-inflammatories, and many others. The efficacy of such agents may be impaired by loss of the agent from the surface to which it is applied. The duration of action of such compositions may therefore be improved by improvements to their substantivity, and this too is addressed by the present invention.

There has now been devised an improved form of oxidative hair dye composition, and related compositions for topical application to various surfaces of the body which overcome or substantially mitigate the above-mentioned and/or other disadvantages of the prior art.

According to a first aspect of the invention, there is provided an oxidative hair dye system comprising a hair dye, an organometallic compound and an oxidising agent.

By "organometallic" in the context of the present invention is meant compounds in which there is a bonding interaction between one or more organic groups or molecules and a main group, transition, lanthanide or actinide metal atom, or metalloid (eg boron, silicon or germanium). An organometallic molecule is usually one which contains a metal-carbon bond. However, in this context, we also include compounds in which the bonding interaction is between one or more other atoms on the organic moiety, eg oxygen atoms. Such organometallic compounds may include inter alia, representatives from the following classes: molecular metal hydrides, metal alkoxides, thiolates, amides, and phosphides, and metal chelates.

The oxidative hair dye system according to the invention is advantageous primarily in that the inclusion of the organometallic compound allows different permanent hair colours and shades to be produced without the use of dye molecules that may be unsafe or toxic (eg PPD). Safer permanent hair colourant compositions may also be produced without the use of ammonia or other noxious alkali materials. The systems according to the present invention may also produce more intense colours than standard oxidative dye combinations, and the colour may be longer-lasting (even without the use of ammonia). These hair dye systems may not need to be applied as frequently to retain the same colour, which is more convenient for the user, saves expense and reduces the potential for hair damage associated with the repeated use of oxidising agents. The systems according to the invention may be milder and gentler on the hair and their use may therefore lead to less hair damage.

In another aspect of the invention, there is provided a method for colouring the hair, which method involves the application to the hair of a hair dye, an organometallic compound and an oxidising agent.

The hair dye, organometallic compound and oxidising agent may be contained in a single formulation, or in two or three separate formulations.

Preferably, the hair dye system comprises two separate formulations, one of which contains the hair dye and the other of which contains the oxidising agent. The organometallic compound may be included in either the formulation containing the hair dye, or the formulation containing the oxidising agent.

The separate formulations may be applied to the hair separately, such that they become mixed on the hair, or more preferably, the separate formulations may be pre-mixed by the user immediately prior to application to the hair.

One preferred class of organometallic compounds that may be utilised in the present invention are organotitanates. Preferred organotitanates are tetraalkyl titanate or titanate chelate compounds of the following general formulae:

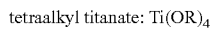
tetraalkyl titanate: Ti(OR)$_4$ titanate chelate

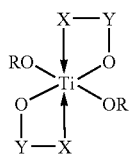

in which

R is a ligand,

X represents a functional group containing oxygen or nitrogen, and

Y represents a two or three carbon chain.

Where the organometallic contains at least one ligand represented by R, preferably each R represents a straight or branched chain $C_{2-20}$ alkyl group. Ligands represented by R in the bonding agent may be the same or different.

Specific examples of suitable tetraalkyl titanates include, but are not restricted to, tetraisopropyltitanate (available under the trade name TYZOR TPT from DuPont de Nemours and Company, LLC), tetra-n-butyltitanate (available from DuPont under the trade name TYZOR TnBT), tetrakis(2-ethylhexyl)titanate (available as TYZOR TOT from DuPont), diisopropyldiisostearyltitanate or other materials which can be described by the general formula Ti(OR)$_4$.

Specific examples of suitable titanate chelates include, but are not restricted to, acetylacetonate titanate chelate (available from DuPont under the trade name TYZOR TPT), ethyl acetoacetate titanate chelate (available from DuPont as TYZOR DC), diisopropyl di-triethanolamino titanate chelate (available from DuPont as TYZOR TE), lactic acid titanate chelate (ammonium salt) (available from DuPont as TYZOR LA) or other materials which can be described by the general formula above.

The most preferred organotitanate is diisopropyl di-triethanolamino titanate chelate.

The concentration of organometallic will typically be in excess of 0.0001% by weight of the overall system (ie as applied to the hair), more commonly in excess of 0.001% by weight of the overall system, and preferably in excess of 0.05% by weight of the overall system. The concentration of the organometallic is preferably less than 10% by weight of the overall system, and preferably less than 1% of the overall system. The concentration of the organometallic may therefore fall in the range 0.0001% to 10% by weight of the overall system, more preferably 0.001% and 1% and most preferably 0.05% to 1% by weight of the overall system.

The hair dye utilised in the present invention may be one or more bases, one or more couplers, or a mixture of bases and couplers. Preferably the hair dye will be selected from the group consisting of bases including p-phenylenediamine, 2,5-diaminotoluene, 2-chloro-p-phenylenediamine, N-phenyl-p-phenylenediamine, N,N-bis(2-hydroxyethyl)-p-phenylenediamine, 3-methyl-4-aminophenol, 2-hydroxyethyl-p-phenylenediamine, p-aminophenol and N-methyl-p-aminophenol, and couplers including resorcinol, 4-chlororesorcinol, 2-methylresorcinol, 1-naphthol, 2-methyl-1-naphthol, 1,5-dihydroxynaphthalene, 1,7-dihydroxynaphthalene, 5-hydroxybenzodioxane, 2,5-dihydroxy-4-methylpyridine, m-aminophenol, 5-amino-2-methylphenol, 5-(2-hydroxyethyl)amino-2-methylphenol, 6-hydroxybenzomorpholine, m-phenylenediamine, 2,4-diaminophenoxyethanol, 2,6-diaminopyridine, 3,3'-dihydroxydiphenylamine o-aminophenol and 2-methyl-5-amino-6-chlorophenol.

More preferably the hair dye will be a mixture of a base and a coupler. A particularly preferred combination of base and coupler is p-aminophenol and 5-amino-o-cresol.

Maximum use levels for all permitted oxidative dyes are specified in The Cosmetics Products (Safety) Regulations 2004 at the time of writing, and must be adhered to. In general, the concentration of hair dye will typically be in excess of 0.001% by weight of the overall system (ie as applied to the hair), and preferably in excess of 0.01% by weight of the overall system. The concentration of the hair dye is preferably less than 10% by weight of the overall system, more commonly less than 5% and preferably less than 3%. The concentration of the hair dye may therefore fall in the range 0.001% to 10% by weight of the overall system, more preferably 0.01% and 5% by weight of the overall system.

The oxidising agent is preferably hydrogen peroxide. Alternatively, the formulation may comprise a compound that, in use, is capable of generating hydrogen peroxide. Examples of the latter class of compounds include urea peroxide (carbamide peroxide), ammonium persulfate and zinc peroxide.

Maximum use levels for hydrogen peroxide, and compounds that release hydrogen peroxide (eg zinc peroxide), are limited under The Cosmetics Products (Safety) Regulations 2004 at the time of writing, and these limits must be adhered to. Other oxidising agents may or may not have specified legal limits. In general, the concentration of oxidising agent will typically be in excess of 0.01% by weight of the overall system (ie as applied to the hair), more commonly in excess of 1% by weight of the overall system, and preferably in excess of 3% by weight of the overall system. The concentration of the oxidising agent is preferably less than 15% by weight of the overall system, and preferably less than 10%. The concentration of the oxidising agent may therefore fall in the range 0.01% to 15% by weight of the overall system, more preferably 1% and 10% and most preferably 3% to 10% by weight of the overall system.

As one can imagine, the cascade of reactions between an oxidising agent and dye is complex, particularly when a combination of bases and couplers are used. It is therefore not surprising that, in many conventional permanent hair dyes, the structures of the final conjugated dye molecules are not fully understood. Hair dyes are routinely formulated to a specific colour by what is essentially a trial and error approach.

The formulations of the present invention have been found to produce more intense colours, longer lasting colours and novel colours and shades compared to conventional oxidative hair dyes. Furthermore, this is achieved without the use of dyes that may be unsafe or toxic (eg PPD), and without using ammonia (or an equivalent harsh alkaline material).

It has been demonstrated that when organotitanates are added to permanent hair dye systems, the resultant colour can be intensified. By the "intensity" of colour is meant, in the context of the present application, the degree of saturation or chroma (according to the Munsell color system). It might have been thought that the greater intensity of colour could be due to more dye remaining on the hair after washing. However, the dye solution itself is visibly more intense in colour after some time has elapsed, suggesting that the formation of the chromophore itself is affected. If the mechanism were simply one in which the dye is more strongly attached to the hair it would be difficult to explain the increase in colour intensity of the solution.

When organometallics are added to a permanent dye system the hue is changed significantly. By "hue" we refer to the attribute of a colour by which it is recognised as a red, a purple, a green etc, and which approximately corresponds to its dominant wavelength. If the action of the organometallic were simply to link more dye to the hair this would be expected to affect the intensity but not the hue.

In conventional permanent dye systems a base dye must be present in order for colour to form. Additional coupler dyes may also be present, but couplers are not used without at least one base. Surprisingly, hair dye systems of the present invention containing only coupler dye molecules (and no base) in admixture with an organometallic and an oxidising agent have been found to generate intense colours. Hues that have, until now, only been possible via use of the base, PPD, (or its derivatives) may thereby be formed without PPD or any other potentially toxic base.

Surprisingly, oxidative hair dye systems of the present invention do not require the inclusion of an additional alkaline material. In particular, systems of the present invention do not require ammonia to perform as improved permanent hair colourants. The addition of an organometallic improves colour durability, even compared to a conventional oxidative hair dye system containing ammonia.

Systems that do not contain ammonia are particularly advantageous because they may be milder, causing less damage to the hair, they may have a more pleasing odour, and may be generally be more pleasant to use. However, in some embodiments of the invention the use of an alkaline material, eg ammonia, may be desirable. Ammonia may be included at levels comparable to the levels used in conventional oxidative hair dyes or, more preferably, ammonia may be present in lower amounts.

The systems of the present invention are suitable for providing additional aesthetic or therapeutic benefits to the hair via the incorporation of other suitable ingredients including conditioners, antioxidants, moisturising agents, proteins, amino acids, vitamins, essential oils, shine agents, sunscreening agents, anti-dandruff actives, perfumes and slip aids, eg silicones.

The formulations used in the present invention comprise an acceptable carrier for the hair dye, the organometallic and any additional benefit ingredients. The selection of suitable carriers is based on the intended product type and the desired sensory and aesthetic properties. The carrier and formulations can be formulated in a number of ways including, but not limited to, emulsions, including oil-in-water, water-in-oil, water-in-oil-in-water, oil-in-water-in-oil, water-in-silicone and oil-in-water-in-silicone emulsions.

In these types of formulation, the range of ingredients in the acceptable carrier can be broad. Such ingredients are typically surfactants, thickeners, sequestering agents, waxes, oils, silicones, gelling agents, pearlising agents, pH adjusting agents, emulsifiers, preservatives, perfumes and colourings.

The formulations may include a surfactant such as cosmetically acceptable salts of alkyl ether sulphates (such as ammonium laureth sulphate or sodium laureth sulphate), alkyl and alkylamidoalkyl betaines (such as cocamidopropyl betaine), ethoxylated alcohols, polyethyleneglycol carboxylates, accepted salts of alkyl sulphates (such as ammonium lauryl sulphate or sodium lauryl sulphate), sulphosuccinates (such as disodium laureth sulphosuccinate), amphoacetates and amphodiacetates (such as disodium cocoamphodiacetates), alkylglucosides and alcohol sulphonates.

The formulations may also include a thickener or viscosity controlling agent such as an amine oxide, block polymers of ethylene oxide and propylene oxide (for examples, those available from BASF Wyandotte under the tradename "Pluronic"®), ethoxylated fatty alcohols, cellulosic derivatives (such as hydroxypropylmethyl cellulose), salt (NaCl), phthalic acid amide, polyvinylalcohols and fatty alcohols, suitably in an amount from about 0.5% to about 10% by weight of the formulation.

The formulations may also include gelling agents such as PVM, MA or a decadienecrosspolymer (available under the trade name Stabilez 06), suitably in an amount from about 0.1% to 2.0% by weight of the formulation.

Sequestering agents may be added to the formulations, such as ethylenediamine tetraacetic acid (EDTA) and salts thereof, suitably in an amount of from about 0.005% to about 0.5% by weight of the formulation.

Also included in the formulations may be waxes such as cocoa butter, suitably in an amount of from about 0.01% to about 1.0% by weight of the formulation.

Pearlising agents may be included, eg stearic monoethanolamine, suitably in an amount from about 0.01% to about 10% by weight of the formulation.

The pH of the formulations is preferably in the range of 8 to 12, more preferably pH 9 to 10.5. To achieve this, the formulation may need to be buffered using means well known in the art, such as a system comprising succinic acid, citric acid, lactic acid and acceptable salts thereof, phosphoric acid, mono- or disodium phosphate and sodium carbonate. The pH may be adjusted with an agent such as sodium hydroxide, aminomethyl propanol, thiethanolamine and caustic potash, suitably in an amount from about 0.01% to about 10% by weight of the formulation.

The ligands of the organotitanate may affect the pH of the formulation and therefore the buffering requirement. For example, the release of triethanolamine upon hydrolysis of Tyzor TE will increase the pH of a hair dye system.

If the formulation is in the form of an emulsion, the emulsifiers used may be any emulsifiers known in the art for use in water-in-oil or oil-in-water emulsions, examples of which follow:

a) sesquioleates such as sorbitan sesquioleate, available commercially for example under the trade name Arlacel 83 (ICI), or polyglyceryl-2-sesquioleate;

b) ethoxylated esters of derivatives of natural oils such as the polyethoxylated ester of hydrogenated castor oil available commercially for example under the trade name Arlacel 989 (ICI);

c) silicone emulsifiers such as silicone polyols available commercially for example under the trade name ABIL WS08 (Th. Goldschmidt AG);
d) anionic emulsifiers such as fatty acid soaps eg potassium stearate and fatty acid sulphates eg sodium cetostearyl sulphate available commercially under the trade name Dehydag (Henkel);
e) ethoxylated fatty alcohols, for example the emulsifiers available commercially under the trade name Brij (ICI);
f) sorbitan esters, for example the emulsifiers available commercially under the trade name Span (ICI);
g) ethoxylated sorbitan esters, for example the emulsifiers available commercially under the trade name Tween (ICI);
h) ethoxylated fatty acid esters such as ethoxylated stearates, for example the emulsifiers available commercially under the trade name Myrj (ICI);
i) ethoxylated mono-, di-, and tri-glycerides, for example the emulsifiers available commercially under the trade name Labrafil (Alfa Chem.);
j) non-ionic self-emulsifying waxes, for example the wax available commercially under the trade name Polawax (Croda);
k) ethoxylated fatty acids, for example the emulsifiers available commercially under the trade name Tefose (Alfa Chem.); and
l) mixtures thereof.

The formulations can be formulated into a wide variety of product types, including shampoos, conditioners, lotions, creams, pastes, sprays, gels, waxes, serums, mousses and tonics. Preferred formulations are easy to apply evenly to the hair, but sufficiently viscous that they do not to run off or drip from the hair once applied. Preferred formulations are therefore formulated into lotions, creams, gels, mousses, shampoos and conditioners.

Permanent hair dye systems of the present invention may initially be in one or more separate formulations (which are combined during use). The product type of separate formulations may be the same or different. Most preferably, there are two formulations that are mixed together prior to application, one being a shampoo- or conditioner-type product containing the dye, and the other a lotion-type product containing the oxidising agent. The organotitanate may be contained in either formulation, and equal or similar volumes of the separate formulations are typically mixed immediately prior to application to wet or dry hair.

In other embodiments, some or all of the components of the system may be supplied as a dry powder mixture. Water is then added immediately prior to use in order to make up the formulation.

The formulations are typically applied to dry hair, and are left on for a pre-determined time whilst the colour develops. This time is preferably between about 1 and 120 minutes. Heat may be applied to speed up colour development.

The hair is then rinsed with water and usually a shampoo and/or conditioner is applied.

In general, strand and patch tests are carried out 48 hours in advance of using an oxidative hair dye product. It may be anticipated that a test patch is developed to specifically check for contact allergies to a particular organometallic and/or hair dye employed in oxidative hair dye formulations of the present invention.

The following experimental results demonstrate the benefits of the present invention, and emphasise the improvements over hair colourants that are currently available.

The values $L^*$, $a^*$ and $b^*$ are those used by CIE (Commission Internationale de l'Eclairage) in the CIELAB colour measurement method. $L^*$ represents the difference between light (where $L^*=100$) and dark (where $L^*=0$), $a^*$ represents the difference between green ($-a^*$) and red ($+a^*$) and $b^*$ represents the difference between yellow ($+b^*$) and blue ($-b^*$). With these co-ordinates, any colour can be defined. Differences in $L^*$, $a^*$, $b^*$ or $E^*$ are represented as $L^*$, $a^*$, $b^*$ or $E^*$, where $E^*=(L^{*2}+a^{*2}+b^{*2})$. $E^*$ represents the magnitude of the difference in colour, but does not indicate the nature of the colour difference.

1. Improved Intensity of Colour Using Standard Dye Combinations

It has been demonstrated that when organotitanates are added to permanent hair dye systems, the resultant colour can be intensified.

Solutions were prepared of p-aminophenol (PAP) and 4-amino-2-hydroxytoluene (also known as 5-amino-o-cresol) (PAOC) at a concentration of 0.25% in water. 10 ml of each solution were added to three 30 ml glass jars, into each of which was suspended a bleached hair swatch. One drop of aqueous hydrogen peroxide solution (30%) was added to each jar, then 1 drop triethanolamine titanate chelate solution (obtained from Dupont as Tyzor TE) was added to one jar only. The jars were sealed and shaken, then left for two hours before the swatches were removed, washed and blow dried. The colour of the swatches was measured using a Minolta calorimeter. The results (colour of hair swatches dyed with oxidative hair dye systems, with and without the addition of an organotitanate) are given in Table 1.

TABLE 1

|  | $L^*$ | $a^*$ | $b^*$ | $\Delta E^*$ |
| --- | --- | --- | --- | --- |
| PAP/PAOC/$H_2O_2$ | 51.43 | 20.92 | 35.80 | 17.34 |
| PAP/PAOC/$H_2O_2$/Tyzor TE | 31.16 | 27.19 | 23.63 | 35.78 |
| Untreated | 82.33 | −0.34 | 13.37 | — |

$\Delta E^*$ gives a measure of colour difference between the untreated and treated swatches, showing that the addition of organotitanate intensifies the colour. It should be noted that the organotitanate used without the presence of additional dyes does not impart much colour to the hair, proving that the organotitanate does not itself act as a dye.

2. Changes in Chromaticity Using Standard Dye Combinations

The data in Table 1 depicts the colour of hair swatches, dyed with and without organotitanate. In particular, $a^*$ and $b^*$ provide information on the hue. Hue ($h_{ab}$) can be expressed quantitatively using the following expression:

$$h_{ab} = \arctan(b^*/a^*)$$

The calculation of the hue of hair swatches dyed with oxidative hair dye systems, with and without the addition of an organotitanate, is shown in Table 2.

TABLE 2

|  | $L^*$ | $a^*$ | $b^*$ | $h_{ab}$ |
| --- | --- | --- | --- | --- |
| PAP/PAOC/$H_2O_2$ | 51.43 | 20.92 | 35.80 | 1.04 |
| PAP/PAOC/$H_2O_2$/Tyzor TE | 31.16 | 27.19 | 23.63 | 0.71 |

It can be seen by comparing the values for $h_{ab}$ in Table 2 that the hue is altered when organotitanate (Tyzor TE) is added.

3. Longer Lasting Colour

Washout tests were performed using the swatches prepared above, by washing each swatch by hand for 30 seconds using a standard shampoo, then rinsing under cold water for 30 seconds. A further swatch, for which 1 drop of ammonia solution was added to the colouring solution, was also included in the test. After each set of 5 washes and rinses the swatches were blow dried and the colour measured using a colorimeter. As the earlier results showed, ΔE* immediately after colouring was not the same for all swatches meaning that it is difficult to compare washout rates using ΔE* directly. Therefore, for each colour measurement, ΔE* was calculated as a percentage of the initial value of ΔE*, allowing the relative rates of colour loss (fade) to be seen. The results are given in Table 3.

TABLE 3

| x | E* after washes and rinses | | | | | |
|---|---|---|---|---|---|---|
| | 0 | 5 | 10 | 15 | 20 | 25 |
| PAP/PAOC/H$_2$O$_2$ | 100.00 | 92.57 | 90.51 | 86.15 | 84.14 | 80.12 |
| PAP/PAOC/H$_2$O$_2$/NH$_3$ | 100.00 | 93.13 | 86.75 | 81.61 | 83.18 | 81.91 |
| PAP/PAOC/H$_2$O$_2$/Tyzor TE | 100.00 | 95.81 | 95.36 | 95.66 | 92.60 | 90.41 |

The results in Table 3 show that the addition of an organotitanate improves colour durability, even compared with an ammonia-containing system.

4. Novel Dye Combinations (Base-Free Colourants)

Usually, a base must be present in order for colour to form. Additional couplers may also be present, but couplers are not used without at least one base. Table 4 shows how the presence of organotitanate causes couplers to act in a similar way to bases. ΔE* gives a measure of colour difference between the untreated and treated swatches.

TABLE 4

| | L* | a* | b* | ΔE* | Colour |
|---|---|---|---|---|---|
| Untreated | 82.3 | −0.3 | 13.4 | — | Blonde |
| PAOC/5A6COC/H$_2$O$_2$ | 75.4 | 4.9 | 31.2 | 1.6 | Blonde |
| PAOC/5A6COC/H$_2$O$_2$/Tyzor TE | 45.3 | 37.9 | 39.8 | 71.2 | Red/orange |
| MAP/H2O2 | 74.5 | 3.2 | 20.3 | 6.2 | Blonde |
| MAP/H2O2/Tyzor TE | 27.2 | 10.8 | 12.8 | 51.5 | Brown |

Two examples are shown, one using a single coupler, m-aminophenol (MAP), the other using PAP and 2-methyl-5-amino-6-chlorophenol (also known as 5-amino-6-chloro-o-cresol) (5A6COC). Clearly, little colour is formed when the coupler is used on its own (as would be expected). However, when the organotitanate is added, intense colour is formed. These are novel combinations of dye molecules, and with the ability to form shades that usually depend on PPD or its derivatives, this offers the possibility of PPD-free, and PPD-derivative-free colourants. It also opens up the possibility that new, improved colours (eg a better red) might be available, which are not possible using conventional combinations of oxidative hair dyes.

It has also been found that organometallic compounds such as those described above, and other related compounds, can confer greater substantivity on topical compositions containing cosmetic or therapeutic benefit agents.

Thus, according to another aspect of the present invention, there is provided a cosmetic composition for topical application to the body, the composition comprising:

a) one or more cosmetic and/or therapeutic benefit agents;

b) a bonding agent having hydrolysable or exchangeable ligands, which will act to covalently link at least one of said benefit agents to a substrate to which the composition is applied; and c) an acceptable carrier.

Such a composition is advantageous primarily in that the composition exhibits improved "substantivity", ie the duration of its effect, long term wear properties and transfer resistance is enhanced.

The bonding agent is a material with a central atom, or atoms, surrounded by ligands which can be cleaved by hydrolysis or removed by exchange with another ligand leaving a reactive substance that serves as a bonding agent between a benefit agent and one or more functional groups that are found in the substrate, eg the skin, hair, nails, lips or mucous membranes. In particular, it has been found that organotitanates, organozirconates or organosilicates serve as suitable bonding agents such that improved substantivity of various benefit agents are observed on the skin, hair, nails, lips or mucous membranes.

Without being limited by theory, it is believed that the bonding agents covalently bond to certain functional groups present in substrates such as skin, hair, nails, lips and mucous membranes to form a substantive attachment of the desired benefit agent to the substrate also containing appropriate functional groups. One embodiment of such a reaction may be represented by the following reaction scheme:

Substrate-A+Active-A+M-(O—R)$_n$→
Substrate-O-M-((OR)$_{n-2}$)O-Active wherein
"Substrate" represents the surface to which the composition is applied, eg skin, hair, nails, lips or mucous membrane,
"Active" represents a benefit agent,
A represents a functional group such as hydroxyl, amino, amido, thio or carboxyl present at the surface of the Substrate or in the Active,
n represents the number of ligands,
M represents titanium, zirconium or silicon, and
R represents a hydrolysable or exchangeable ligand.

It will be appreciated that the ligands R involved, and the functional groups A, may all be the same, or may be different.

The bonding agent utilised in the present invention is preferably an organotitanate, organozirconate or organosilicate, more preferably a tetraalkyl titanate or titanate chelate, of the following general structures:

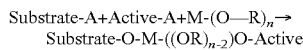
tetraalkyl titanate: Ti(OR)$_4$ titanate chelate:

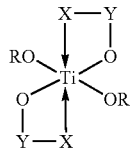

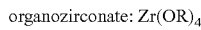
organozirconate: Zr(OR)$_4$

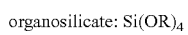
organosilicate: Si(OR)$_4$ in which
R is a ligand,
X represents a functional group containing oxygen or nitrogen, and
Y represents a two or three carbon chain.

Where the bonding agent contains at least one ligand represented by R, preferably each R represents a straight or branched chain $C_{2-20}$ alkyl group. Ligands represented by R in the bonding agent may be the same or different.

The bond between the ligand and central atom may be susceptible to hydrolysis and under appropriate conditions can be cleaved to leave a reactive material which can act as a bonding agent by reacting with functional groups on a substrate and benefit agent. One such hydrolysis reaction is represented by the following scheme:

$$Ti(OR)_4 + H_2O \rightarrow Ti(OR)_3OH + ROH$$

$$Ti(OR)_3OH + Ti(OR)_4 \rightarrow (RO)_3TiOTi(OR)_3 + ROH$$

$$(RO)_3TiOTi(OR)_3 + 2H_2O \rightarrow 2[HOTi(OR)_2OH] + 2ROH$$

$$HOTi(OR)_2OH \rightarrow TiO_2 \cdot 2H_2O + 4ROH$$

In the presence of a substrate and active with appropriate functional groups (in this example, hydroxyl), the following type of reaction can occur:

$$Ti(OR)_4 + Substrate\text{-}OH \rightarrow Substrate\text{-}O\text{---}Ti(OR)_3 + ROH$$

$$Substrate\text{-}O\text{---}Ti(OR)_3 + HO\text{-}Active \rightarrow Substrate\text{-}O\text{---}Ti(OR)_2\text{---}O\text{-}Active$$

The reaction above involves a tetraalkyl titanate, and similar representations could be proposed for the other types of bonding agents referred to herein.

Alternatively, the ligand may be exchanged with other ligands by a mechanism not involving hydrolysis, leaving a reactive material which can act to covalently link benefit agents to a substrate.

In another aspect of the present invention, there is provided a method for improving the substantivity of a benefit agent, which method involves the application to a substrate of separate compositions, one of which contains a bonding agent as described above, and the other of which contains the benefit agent, such that the separate compositions become mixed on the substrate.

The present invention uses the bonding agent(s) in amounts that are safe and efficacious. By "safe and efficacious amount" is meant an amount that is sufficient to confer a perceptible and/or significant benefit, but low enough to avoid any significant side effects, as would be judged by someone who is skilled in the art. As used herein, "cosmetic benefit agent" means a compound, material, and/or active that confers an aesthetic, sensory or functional attribute to the surface of the substrate, in particular skin, hair, nails, lips or mucous membranes to which it is applied. Similarly, "therapeutic benefit agent" means a compound, material, and/or active that has a therapeutic effect on the surface of the substrate to which it is applied, or which has a therapeutic effect elsewhere in the body when delivered via that substrate.

Preferred bonding agents for use in this aspect of the present invention are tetraalkyl titanate or titanate chelate compounds of the general formulae:

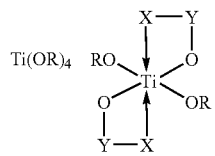

wherein R, X and Y are as defined above.

Specific examples include, but are not restricted to, acetylacetonate titanate chelate (available from DuPont under the trade name TYZOR TPT), ethyl acetoacetate titanate chelate (available from DuPont as TYZOR DC), triethanolamine titanate chelate (available from DuPont as TYZOR TE), lactic acid titanate chelate (ammonium salt) (available from DuPont as TYZOR LA) or any other material which can be described by the general formula above.

Other bonding agents that may be useful are organozirconate and organosilicate compounds of the following general types:

Organozirconate $$Zr(OR)_4$$

wherein R is as defined above.

Specific examples include, but are not restricted to, zirconium tetra-n-butanolate, zirconium tetra-n-propanolate, or any other material which can be described by the general formula $Zr(OR)_4$.

Organosilicate $$Si(OR)_4$$

wherein R is as defined above.

Specific examples include, but are not restricted to, tetraethylorthosilicate or any material which can be described by the general formula $Si(OR)_4$.

The composition according to the invention preferably comprises from about 0.001% to about 25%, by weight of the composition, of the bonding agent, and more preferably from about 0.1% to about 10%.

The composition of the present invention is suitable for providing therapeutic or aesthetic benefits by deposition and adhesion to skin, hair, nails, lips or mucous membranes. Suitable cosmetic agents include, but are not limited to those selected from the group consisting of absorbents, anti-cellulite agents, anti-dandruff agents, anti-oxidants, antiperspirant/deodorant actives, antiseborrhoeic agents, anti-skin atrophy actives, anti-wrinkle actives, artificial tanning agents and accelerators, astringents, bactericides, barrier repair agents, binders, bleaching agents, buffering agents, bulking agents, carotenoids, chelating agents, cicatrizing agents, colorants, dyes, elastomers, emollients, enzymes, essential oils, fatty acids, film formers, flavours, fragrances, freshening products, hair conditioners, hormones, humectants, hydrocolloids, insect repellents, keratolytic agents, light diffusers, nail enamels, oil absorbers, opacifying agents, optical brighteners, optical modifiers, oxidizing agents, particulates, perfumes, pH adjusters, pigments, plant tissue extracts, reducing agents, resins, retinoids, sebum regulators, sequestering agents, skin conditioners/moisturisers, skin feel modifiers, skin protectants, skin treating agents, skin exfoliating agents, skin lightening agents, skin soothing and/or healing agents, skin thickeners, styling agents, tonics, water soluble and liposoluble sunscreen actives, UV stabilisers, vitamin compounds, and combinations thereof. Suitable therapeutic benefit agents include, but are not limited to, those selected from the group consisting of anti-acne agents, anti-fungal agents, anti-inflammatory agents, anti-microbial agents, topical anaesthetics and anti-viral agents.

Suitable colorants include those used in foundations, blushes, blemish covering compositions, and other typical color cosmetic products. Such agents, in effect, result in cosmetic compositions that are suitable for make-up application.

The compositions of the present invention comprise a cosmetically- or pharmaceutically-acceptable carrier or vehicle for the bonding agent and benefit agent and any additional components. The selection of suitable carriers is based on the intended application of the composition. The carrier and compositions can be formulated in a number of ways, including but not limited to emulsions, including oil-in-water, water-in-oil, water-in-oil-in-water, oil-in-water-in-oil, water-in-silicone and oil-in-water-in-silicone emulsions.

The compositions of the present invention can be formulated into a wide variety of product types, including creams, waxes, pastes, putty, lotions, milks, mousses, gels, oils, tonics, and sprays. Preferred compositions are formulated into lotions, creams, gels, sprays, lipsticks and lip glosses. These product forms may be used for a number of applications, including, but not limited to, hand and body lotions, cold creams, facial moisturisers, anti-acne preparations, topical analgesics, make-ups/cosmetics including foundations, eye-shadows, lip cosmetics, and the like. Any additional components required to formulate such products vary with product type and can be routinely chosen by one skilled in the art.

The compositions of the present invention are useful in a variety of applications involving the skin, hair, nails, lips and mucous membranes, depending on the nature of the benefit agent that is attached using the bonding agent. The methods of use for the compositions disclosed and claimed herein include, but are not limited to, methods of increasing the substantivity of a cosmetic active to skin, methods of moisturising skin, methods of improving the natural appearance of skin, methods of applying a colour cosmetic to skin or lips, methods of deodorizing skin, methods of providing antiperspirant efficacy to skin, methods of preventing, retarding, and/or treating wrinkles, methods of providing UV protection to skin, methods of preventing, retarding, and/or treating cellulite, methods of preventing, retarding, and/or controlling the appearance of oil, methods of modifying the feel and texture of skin, methods of providing even skin tone, methods of concealing blemishes and/or imperfections in human skin methods of preventing or treating skin malodour, methods of colouring hair, methods of styling hair and methods of conditioning the hair.

The invention will now be described in greater detail, by way of illustration only, with reference to the following Examples, in which Examples 1 to 3 are illustrative of oxidative hair dyes, and Examples 4 to 18 relate to topical compositions with improved substantivity. The type and amount of hair dye to be incorporated into the oxidative hair dyes according to the invention will depend on the colorant effect desired.

EXAMPLE 1

Surfactant (shampoo) base component containing the hair dye and organometallic

|     | Ingredient | % w/w |
| --- | --- | --- |
| 1.  | Cocamide MEA | 3.5 |
| 2.  | Glycol distearate | 3.5 |
| 3.  | Sodium gluceptate | 0.25 |
| 4.  | Sodium metabisulfate | 2.0 |
| 5.  | Sodium erbthroborate | 0.3 |
| 6.  | Cocamidopropyl betaine | 6.625 |
| 7.  | Dilute sodium lauryl-ether sulfate | 25.75 |
| 8.  | Laureth-3 | 10 |
| 9.  | Oleic acid | 4 |
| 10. | Ammonia | 3.5 |
| 11. | Citric acid monohydrate | 0.1 |
| 12. | Hair dyes | qs |
| 13. | Organotitanate | qs |
| 14. | Purified water to | 100% |

Method

1. Heat 1, 2 & 8 to 70-75° C., until melted.
2. Disperse 3, 4, 5, 11 & 12 into 14 and heat to 70-75° C.
3. Stir in 6 & 7, to water phase, and maintain at 70-75° C.
4. Add oils phase to water phase and homogenise for 10 minutes.
5. Cool to <35° C.
6. Stir in 9 & 10 slowly.

EXAMPLE 2

Emulsion (conditioner) base component containing the hair dye and organometallic

| Ingredients | % w/w |
| --- | --- |
| 1. Tetra sodium EDTA | 0.14 |
| 2. Sodium Benzoate | 0.1 |
| 3. Phenoxyethanol | 0.1 |
| 4. Citric asid monohydrate | 1.5 |
| 5. Ceteath-25 | 1.5 |
| 6. Cetearyl alcohol | 2.25 |
| 7. Stearyl alcohol | 2.25 |
| 8. Hair dyes | qs |
| 9. Organotitanate | qs |
| 10. Purified water | to 100% |

Method

1) Heat 5, 6 & 7 to 70-75° C.
2) Disperse 1, 2 & 8 into 9. Heat to 70-75° C.
3) Add oils to water phase and homogenise for 10 minutes.
4) Cool to <35° C.
5) Stir in 3.

EXAMPLE 3

Developing lotion component containing the oxidising agent

| Ingredients | % w/w |
| --- | --- |
| 1. Tetra sodium EDTA | 0.1 |
| 2. Phosphoric acid | 0.1 |
| 3. Hydrogen peroxide solution (65%) | 25.0 |
| 4. Ceteath-20 | 2.0 |
| 5. Cetearyl alcohol | 4.0 |
| 6. Sodium Stannate | 0.005 |
| 7. Purified water | to 100% |

Method

1. Disperse 1, 2 & 6 into 7. Heat to 70-75° C.
2. Heat 4 & 5 to 70-75° C. until melted.
3. Add oils to water and homogenise for 10 minutes.
4. Cool to <35° C.
5. Stir in 3, followed by 7.

In use, a suitable product combination would be the shampoo or conditioner base product (eg the formulation of Example 1 or Example 2) carrying the hair dye molecules and the organometallic, and the developing lotion (eg the formulation of Example 3) that delivers the oxidising agent. The organometallic may be included in the developing lotion with the oxidising agent, but is more preferably in the base formulation that carries the hair dye. Typically, equal volumes of the base formulation and the developing lotion are mixed together to initiate reaction. This mixture is then applied to dry hair for any time from about 1 minute to about 120 minutes. The hair is then rinsed with water and usually a shampoo or conditioner is used. The hair is then allowed to dry naturally, or may be dried by towel or with the use of a hair dryer.

EXAMPLE 4

Two areas of human skin were treated using Blue No 1 Dye, one of which had previously had applied to it an amount of tetra n-butyl titanate. One minute after the dye had been applied it was washed from the skin using soap and water. The blue colour was visibly more intense where the tetra n-butyl titanate had been applied, and was longer lasting than the colouration of the control (untreated) area.

EXAMPLE 5

Two swatches of human hair were treated using olive oil, one of which had previously had applied to it an amount of tetra n-butyl titanate. One minute after the oil had been applied it was washed from the hair using soap and water. The hair which had been treated with tetra n-butyl titanate was noticeably more oily than the control (untreated) swatch. Surprisingly the oil could not be removed even after several washes using sodium lauryl sulphate.

EXAMPLE 6

Day Cream

|  | % w/w |
|---|---|
| Aqua | to 100 |
| Butylene glycol | 5 |
| Dicaprylyl maleate | 4 |
| *Paraffinum liquidum* | 4 |
| Octyl methoxycinnamate | 3 |
| Petrolatum | 3 |
| Cetyl Alcohol | 2 |
| Glycerin | 2 |
| Dimethicone | 2 |
| Cetearyl alcohol | 1.6 |
| Butyl methoxydibenzoylmethane | 1 |
| Hydroxyethylcellulose | 0.4 |
| PEG-20 stearate | 0.4 |
| Polyacrylamide | 0.4 |
| Parfum | 0.3 |
| C13-14 isoparaffin | 0.215 |
| Retinyl palmitate | 0.15 |
| Tetrasodium EDTA | 0.1 |
| Citric acid | 0.08 |
| Laureth-7 | 0.055 |
| BHT | 0.0024 |
| Lactic acid titanate chelate, ammonium salt | 1 |
| Preservative | q.s |

Stage 1
Tetrasodium EDTA and citric acid are added to the water using a propellor stirrer. The hydroxyethylcellulose is added and dispersed using a homogeniser, butylene glycol, glycerin and methylparaben are added and the bulk is heated to 70° C.

Stage 2
The dicaprylyl maleate, paraffinum liquidum, octyl methoxycinnamate, petrolatum, cetyl alcohol, dimethicone, cetearyl alcohol, butyl methoxydibenzoylmethane, PEG-20 stearate, C13-14 isoparaffin, laureth-7 and BHT are mixed and heated to 70° C. to melt the waxes.

Stage 3
Using a homogeniser, stage 2 is added to stage 1 and the bulk is mixed until emulsified and stable. The product is then cooled to below 35° C. using stirring. The remaining raw materials, including the lactic acid titanate chelate, ammonium salt solution are added and the product is mixed using a propellor stirrer until uniform. The product is made to weight using purified water.

This formulation gives long lasting moisturing benefits.

EXAMPLE 7

Night Cream

|  | % w/w |
|---|---|
| Aqua | to 100 |
| Glycerin | 5 |
| *Paraffinum liquidum* | 4.5 |
| Dicaprylyl maleate | 3 |
| Dimethicone | 3 |
| Petrolatum | 3 |
| Paraffin | 2.9 |
| Cetyl alcohol | 2 |
| Steareth-2 | 2 |
| Glyceryl stearate | 1.5 |
| *Butyrospermum parkii* | 1.5 |
| Steareth-21 | 1 |
| Mannitol | 1 |
| *Cera microcristallina* | 0.262 |
| *Buxus chinensis* | 0.5 |
| Propylene glycol | 0.48 |
| Parfum | 0.4 |
| *Borago officinalis* | 0.3 |
| Hydroxyethylcellulose | 0.3 |
| *Lactis proteinum* | 0.3 |
| Xanthan gum | 0.25 |
| Alcohol denat. | 0.08 |
| Sodium citrate | 0.08 |
| Lecithin | 0.075 |
| BHT | 0.05 |
| Faex | 0.04 |
| Phospholipids | 0.03 |
| Citric acid | 0.025 |
| Lactic acid titanate chelate, ammonium salt solution | 1 |
| Preservative | q.s |

Stage 1
Into the water, the citric acid and sodium citrate are added and dispersed. The hydroxyethylcellulose is added and hydrated using a propellor stirrer. Xanthan gum is pre-dispersed in glycerin and added to the bulk. This is stirred until uniform. The aqueous phase is then heated to 70° C.

Stage 2
The paraffinum liquidum, dicaprylyl maleate, dimethicone, petrolatum, paraffin, cetyl alcohol, steareth-2, glyceryl stearate, steareth-21, cera microcristallina and BHT are mixed and heated to 70° C. to melt the waxes.

Stage 3
Using a homogeniser, stage 2 is added to stage 1 and this is mixed until emulsified and uniform. The emulsion is then cooled to below 35° C. using stirring. The remaining materials, including the lactic acid titanate chelate, ammonium salt solution are then added and mixed. The product is then made to weight using purified water and is stirred until uniform.

This formulation gives long lasting skin benefits such as moisturisation.

EXAMPLE 8

Eye Cream

|  | % w/w |
|---|---|
| Aqua | to 100 |
| Butylene glycol | 6 |
| *Paraffinum liquidum* | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| *Prunus dulcis* | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| Lactic acid titanate chelate, ammonium salt solution | 1 |
| Preservative | q.s |

Stage 1

Into the water, citric acid, EDTA, sodium phosphate, disodium phosphate and lactic acid are added and dispersed. Using a homogeniser, carbomer is added and hydrated. The aqueous phase is then heated to 70° C.

Stage 2

The paraffinum liquidum, octyl methoxycinnamate, dimethicone, petrolatum, cetearyl octanoate, cetearyl alcohol, glyceryl stearate, cetyl alcohol, hydrogenated vegetable glycerides citrate, tocopheryl acetate, PEG-20 stearate, isopropyl myristate and PEG-12 isostearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the lactic acid titanate chelate, ammonium salt solution are then added and mixed. The product is then made to weight using purified water and is stirred until uniform.

This formulation gives long lasting benefits to the area surrounding the eyes

EXAMPLE 9

Eye Cream

|  | % w/w |
|---|---|
| Aqua | to 100 |
| Butylene glycol | 6 |
| *Paraffinum liquidum* | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| *Prunus dulcis* | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| Lactic acid titanate chelate, ammonium salt solution | 10 |
| Preservative | q.s |

Stage 1

Into the water, citric acid, EDTA, sodium phosphate, disodium phosphate and lactic acid are added and dispersed. Using a homogeniser, carbomer is added and hydrated. The aqueous phase is then heated to 70° C.

Stage 2

The paraffinum liquidum, octyl methoxycinnamate, dimethicone, petrolatum, cetearyl octanoate, cetearyl alcohol, glyceryl stearate, cetyl alcohol, hydrogenated vegetable glycerides citrate, tocopheryl acetate, PEG-20 stearate, isopropyl myristate and PEG-12 isostearate are mixed and heated to 7° C. to melt the waxes.

Stage 3

Using a homogeniser, stage 2 is added to stage 1 and this is mixed until emulsified and uniform. The emulsion is then cooled to below 35° C. using stirring. The remaining materials, including the lactic acid titanate chelate, ammonium salt solution are then added and mixed. The product is then made to weight using purified water and is stirred until uniform.

This formulation gives long lasting benefits to the area surrounding the eyes

EXAMPLE 10

Skin Protection Lotion

|  | % w/w |
|---|---|
| Aqua | to 100 |
| Dimethicone | 5 |
| Glycerin | 3 |
| Kaolin | 3 |
| Dicaprylyl maleate | 2.5 |
| Isopropyl myristate | 2.5 |
| Stearate-2 | 2 |
| Octyl methoxycinnamate | 1 |
| Steareth-21 | 1 |
| Cetyl alcohol | 0.75 |
| Butyl methoxydibenzoylmethane | 0.5 |
| Propylene glycol | 0.5 |
| Hydroxyethylcellulose | 0.4 |
| Xanthan gum | 0.24 |
| Serica | 0.1 |
| Sodium C8-16 isoalkylsuccinyl lactoglobulin sulfonate | 0.1 |
| Tetrasodium EDTA | 0.1 |
| Citric acid | 0.05 |
| Lactic acid titanate chelate, ammonium salt solution | 1 |
| Preservative | q.s |

Stage 1
Into the water, the citric acid and EDTA are added and dispersed. The hydroxyethylcellulose is added and hydrated using a propeller stirrer. Xanthan gum is pre-dispersed in glycerin and added to the bulk. This is stirred until uniform. The aqueous phase is then heated to 70° C.

Stage 2
The dimethicone, dicaprylyl maleate, isopropyl myristate, stearate-2, octyl methoxycinnamate, steareth-21, cetyl alcohol and butyl methoxydibenzoylmethane are mixed and heated to 70° C. to melt the waxes.

Stage 3
Using a homogeniser, stage 2 is added to stage 1 and this is mixed until emulsified and uniform. The emulsion is then cooled to below 35° C. using stirring. The remaining materials, including the lactic acid titanate chelate, ammonium salt solution are then added and mixed. The product is then made to weight using purified water and is stirred until uniform.

This formulation gives long lasting skin benefits.

EXAMPLE 11

Sun Lotion SPF8

|  | % w/w |
|---|---|
| Aqua | to 100 |
| C12-15 Alkyl Benzoate | 8 |
| Butylene glycol | 5 |
| Butyl methoxydibenzoylmethane | 2.2 |
| Dimethicone | 2 |
| Polyglyceryl-3 methylglucose distearate | 2 |
| PVP/hexadecene copolymer | 1.75 |
| Octyl methoxycinnamate | 1.7 |
| *Theobroma cacao* | 0.5 |
| Parfum | 0.5 |
| Tocopheryl acetate | 0.2 |
| Acrylates/vinyl isodecanoate crosspolymer | 0.15 |
| Potassium hydroxide | 0.034 |
| Tetrasodium EDTA | 0.02 |
| Preservative | q.s |
| Lactic acid titanate chelate, ammonium salt solution | 10 |

Stage 1
The EDTA is dispersed into the water. Using a propellor stirrer, the acrylates/vinyl isodecanoate crosspolymer are added and dispersed and hydrated. Butylene glycol is added and the aqueous phase is heated to 70° C.

Stage 2
The C12-15 alkyl benzoate, butyl methoxydibenzoylmethane, dimethicone, polyglyceryl-3 methylglucose distearate, PVP/hexadecene copolymer, octyl methoxycinnamate, theobroma cacao and tocopheryl acetate are mixed and heated to 70° C. to melt the waxes.

Stage 3
Using a homogeniser, stage 2 is added to stage 1 and the bulk is mixed until emulsified and uniform. The emulsion is cooled to below 35° C. with stirring. The remaining materials, including the lactic acid titanate chelate, ammonium salt solution are added and mixed. The product is made to weight using purified water and stirred until uniform.

This formulation gives long lasting protection from UV radiation.

EXAMPLE 12

Anti-Ageing Foundation

|  | % w/w |
|---|---|
| Aqua | to 100 |
| Butylene glycol | 9.8 |
| Cetearyl isononanoate | 4.9 |
| Dimethicone | 3.2 |
| Glycerin | 1.96 |
| Silica | 1.9 |
| Caprylic/capric triglyceride | 1.67 |
| *Paraffinum liquidum* | 1.67 |
| Petrolatum | 1.67 |
| Hydrogenated coco-glycerides | 1.67 |
| Cetearyl octanoate | 1.5 |
| Cetearyl alcohol | 1.35 |
| Octyl methoxycinnamate | 1.28 |
| Talc | 1 |
| Glyceryl stearate | 0.95 |
| PEG-100 stearate | 0.9 |
| Butyl methoxydibenzoylmethane | 0.6 |
| Saccharide isomerate | 0.54 |
| Lactic acid | 0.45 |
| Sodium polyacrylate | 0.45 |
| Boron nitride | 0.42 |
| Sodium PCA | 0.4 |
| *Borago officinalis* | 0.4 |
| Tocopheryl acetate | 0.4 |
| PVP/hexadecene copolymer | 0.4 |
| PEG-20 stearate | 0.33 |
| Glycolic acid | 0.2 |
| Sodium stearoyl lactylate | 0.2 |
| Isopropyl myristate | 0.17 |

-continued

|  | % w/w |
| --- | --- |
| Polyaminopropyl biguanide | 0.16 |
| Tetrasodium EDTA | 0.1 |
| Xanthan gum | 0.1 |
| Citric acid | 0.06 |
| Alcohol denat. | 0.04 |
| Lecithin | 0.037 |
| Preservative | q.s |
| Lactic acid titanate chelate, ammonium salt solution | 10 |

Stage 1

Into the water, citric acid, EDTA and Lactic acid are added and dispersed. Xanthan gum is pre-dispersed in butylene glycol and is added to the bulk. The aqueous phase is then heated to 70° C.

Stage 2

The cetearyl isononanoate, dimethicone, Silica, PVP/hexadecene copolymer, caprylic/capric triglyceride, paraffinum liquidum, petrolatum, hydrogenated coco-glycerides, cetearyl octanoate, cetearyl alcohol, octyl methoxycinnamate, talc, glyceryl stearate, PEG-100 stearate, butyl methoxydibenzoylmethane, borago officinalis, tocopheryl acetate, sodium stearoyl lactylate, isopropyl myristate and lecithinoil phase are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the lactic acid titanate chelate, ammonium salt solution are then added and mixed. The product is then made to weight using purified water and is stirred until uniform.

This formulation gives long lasting anti ageing benefits to the skin.

EXAMPLE 13

Lipstick

|  | % w/w |
| --- | --- |
| *Ricinus communis* | 20 |
| Octyldodecanol | 15 |
| Pentaerythrityl tetracaprylate/caprate | 14 |
| Mica | 10 |
| Bis-diglyceryl caprylate/caprate/isostearate/Stearate/hydroxystearate adipate | 7.5 |
| Paraffin | 5 |
| Cera microcristallina | 5 |
| Propylene glycol | 2 |
| Hydrogenated castor oil | 2 |
| Candelilla cera | 1 |
| Carnauba | 1 |
| Synthetic wax | 1 |
| *Butyrospermum parkii* | 1 |
| Titanium dioxide | 0.5 |
| Tocopheryl acetate | 0.2 |
| Polyquaternium-37 | 0.2 |
| Red colour | q.s |
| Tetra n-butyl titanate | 1 |

Stage 1

The tetra n-butyl titanate is pre-dispersed in propylene glycol, with stirring.

Stage 2

The remaining materials are mixed in a vessel and heated to 85° C. until melted and uniform. The product is cooled and the tetra n-butyl titanate pre-mix is added below 70° C. The product poured into a suitable container and allowed to cool to room temperature to set.

This formulation provide lipstick that is long lasting and without dryness.

EXAMPLE 14

Lipstick

|  | % w/w |
| --- | --- |
| *Ricinus communis* | 20 |
| Octyldodecanol | 15 |
| Pentaerythrityl tetracaprylate/caprate | 14 |
| Mica | 10 |
| Bis-diglyceryl caprylate/caprate/isostearate/Stearate/hydroxystearate adipate | 7.5 |
| Paraffin | 5 |
| Cera microcristallina | 5 |
| Propylene glycol | 2 |
| Hydrogenated castor oil | 2 |
| Candelilla cera | 1 |
| Carnauba | 1 |
| Synthetic wax | 1 |
| *Butyrospermum parkii* | 1 |
| Titanium dioxide | 0.5 |
| Tocopheryl acetate | 0.2 |
| Polyquaternium-37 | 0.2 |
| Red colour | q.s |
| Tetra n-butyl titanate | 10 |

Stage 1

The tetra n-butyl titanate is pre-dispersed in propylene glycol, with stirring.

Stage 2

The remaining materials are mixed in a vessel and heated to 85° C. until melted and uniform. The product is cooled and the tetra n-butyl titanate pre-mix is added below 70° C. The product poured into a suitable container and allowed to cool to room temperature to set.

This formulation provide lipstick that is long lasting and without dryness.

EXAMPLE 15

Hair Conditioner

|  | % w/w |
| --- | --- |
| Aqua | to 100 |
| Cetyl alcohol | 3 |
| Cetrimonium chloride | 0.8 |
| Hydroxyethylcellulose | 0.6 |
| Propylene glycol | 0.5 |
| Panthenol | 0.5 |
| Parfum | 0.3 |
| Benzophenone-4 | 0.2 |
| Sodium chloride | 0.1 |
| Wheat amino acids | 0.14 |
| Citric acid | 0.02 |
| Tetrasodium EDTA | 0.02 |
| Lactic acid titanate chelate, ammonium salt solution | 1 |

Stage 1

The EDTA and Hydroxyethylcellulose were added to the water and mixed using a homogeniser to hydrate the polymer. Citric acid, Benzophenone and Cetrimonium chloride were added. This was then heated to 70° C.

Stage 2

Cetyl alcohol was heated to 70° C. in a separate vessel.

Stage 3

The melted cetyl alcohol was then added to stage 1 using a homogeniser.

Stage 4

The mixture was then cooled to below 40° C. using a prop. stirrer. The remaining materials including the lactic acid titanate chelate, ammonium salt solution were then added and the product was made to weight with purified water.

This formulation gives long lasting conditioning benefits to the hair.

EXAMPLE 16

Intensive Conditioner

|  | % w/w |
| --- | --- |
| Aqua | to 100 |
| Cetearyl alcohol | 4.5 |
| Arachidyl propionate | 2 |
| Dimethicone | 2 |
| Panthenol | 0.75 |
| Stearamidopropyl dimethylamine | 1.5 |
| Hydroxyethylcellulose | 0.5 |
| Amodimethicone | 0.7 |
| Citric acid | 0.5 |
| Cetrimonium chloride | 0.4 |
| PEG-20 stearate | 0.4 |
| Parfum | 0.3 |
| Propylene glycol | 0.3 |
| Benzophenone-4 | 0.2 |
| Sodium chloride | 0.15 |
| Wheat amino acids | 0.15 |
| Polyquaternium-39 | 0.1 |
| Lactic acid titanate chelate, ammonium salt solution | 1 |

Stage 1

The EDTA and HEC were added to the water and mixed using a homogeniser to hydrate the polymer.

Stage 2

The citric acid and cetrimonium chloride were added and mixed using a prop. Stirrer. The mixture was then heated to 70° C.

Stage 3

In a separate vessel, the waxes, dimethicone and BHT were mixed and heated to 70° C. until melted and uniform.

Stage 4

Stage 3 was added to stage 2 and this was mixed until uniform. The mixture was then cooled to below 40° C. with stirring.

Stage 5

The remaining materials including the lactic acid titanate chelate, ammonium salt solution were then added and the product was made to weight using purified water.

This formulation gives long lasting conditioning benefits to the hair.

EXAMPLE 17

Leave-in Conditioner

|  | % w/w |
| --- | --- |
| Aqua | to 100 |
| PEG-40 hydrogenated castor oil | 2 |
| Dipropylene glycol | 1 |
| Phenoxyethanol | 0.8 |
| Parfum | 0.3 |
| Panthenol | 0.4 |
| Propylene glycol | 0.25 |
| Methylparaben | 0.2 |
| Benzophenone-4 | 0.2 |
| Lactic acid titanate chelate, ammonium salt solution | 1 |

Stage 1

The Polyquaternium-10 was added to the water and hydrated using a prop. stirrer.

Stage 2

The Methylparaben was pre-dispersed in Dipropylene glycol, gently heated to melt and then added to stage 1.

Stage 3

The remaining materials including the lactic acid titanate chelate, ammonium salt solution were then added and the product was mixed and made to weight with purified water.

This formulation gives long lasting conditioning benefits to the hair.

EXAMPLE 18

Antidandruff Shampoo

|  | % w/w |
| --- | --- |
| Aqua | to 100 |
| Sodium laureth sulfate | 6 |
| Disodium laureth sulfosuccinate | 4 |
| Laureth-3 | 3 |
| Cocamidopropyl betaine | 2.5 |
| Sodium chloride | 2 |
| Dipropylene glycol | 1 |
| Parfum | 0.5 |
| Piroctone olamine | 0.5 |
| Panthenol | 0.4 |
| Propylene glycol | 0.3 |
| Disodium phosphate | 0.25 |
| Benzophenone-4 | 0.2 |
| Wheat amino acids | 0.15 |
| Lactic acid titanate chelate, ammonium salt solution | 1 |

Stage 1

EDTA, Citric acid and Benzophenone-4 were added and mixed into the water. Sodium laureth sulfate, Disodium laureth sulfosuccinate and Dipropylene glycol were then added.

Stage 2

Disodium phosphate, wheat amino acids and the lactic acid titanate chelate, ammonium salt solution were added and the product was stirred until uniform.

Stage 3

The Piroctone olamine was dispersed in the parfum and added to the Laureth-3. This mixture was added to the bulk and stirred.

Stage 4

The remaining materials were then added and the product was made to weight with purified water.

This formulation gives long lasting anti-dandruff benefits to the hair.

The invention claimed is:

1. An oxidative hair dye system comprising a hair dye, an organotitanate compound and an oxidising agent.

2. An oxidative hair dye system as claimed in claim 1, wherein the organotitanate is a tetraalkyl titanate described by the general formula Ti(OR)$_4$ wherein each ligand represented by R is a straight or branched chain $C_{2-20}$ alkyl group.

3. An oxidative hair dye system as claimed in claim 1, wherein the organotitanate is a titanate chelate compound described by the general formula:

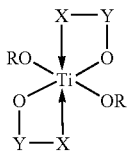

in which
each ligand represented by R is a straight or branched chain $C_{2-20}$ alkyl group,
X represents a functional group containing oxygen or nitrogen, and
Y represents a two or three carbon chain.

4. An oxidative hair dye system as claimed in claim 1, wherein the or organotitanate is a tetraalkyl titanate is selected from the group consisting of tetraisopropyltitanate, tetra-n-butyltitanate, tetrakis(2-ethylhexyl)titanate and diisopropyldiisostearyltitanate.

5. An oxidative hair dye system as claimed in claim 1, wherein the or organotitanate is a titanate chelate compound selected from the group consisting of acetylacetonate titanate chelate, ethyl acetoacetate titanate chelate, diisopropyl di-triethanolamino titanate chelate and lactic acid titanate chelate (ammonium salt).

6. An oxidative hair dye system as claimed in claim 1, wherein the concentration of the organotitanate compound is in the range 0.0001% to 10% by weight of the overall system.

7. An oxidative hair dye system as claimed in claim 1, wherein the hair dye comprises a mixture of one or more bases and one or more couplers.

8. An oxidative hair dye system as claimed in claim 1, wherein the concentration of hair dye is in the range 0.001% to 10% by weight of the overall system, and/or the concentration of oxidizing agent is in the range 0.01% to 15% by weight of the overall system.

9. A method of colouring the hair, which method involves the application to the hair of an oxidative hair dye system as claimed in claim 1.

10. A cosmetic composition for topical application to the body, comprising:
a) one or more cosmetic and/or therapeutic benefit agents;
b) a bonding agent having hydrolysable or exchangeable ligands selected from the group consisting of organotitanates, organozirconates and organosilicates, which will act to covalently link at least one of said benefit agents to a substrate to which the composition is applied; and
c) an acceptable carrier.

11. A composition as claimed in claim 10, wherein the bonding agent is a tetraalkyl titanate or titanate chelate selected from the group consisting of:
tetraalkyl titanates of general formula

titanate chelates of the general formula

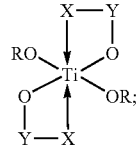

organozirconates of the general formula

and
organosilicates of the general formula

in which
each R independently represents a straight or branched chain $C_{2-20}$ alkyl group,
X represents a functional group containing oxygen or nitrogen, and
Y represents a two or three carbon chain.

12. A composition as claimed in claim 10, wherein the bonding agent is a tetraalkyl titanate compound of the formula:

wherein each R independently represents a straight or branched $C_{2-20}$ alkyl group.

13. A composition as claimed in claim 10, wherein the bonding agent is selected from the group consisting of tetraisopropyltitanate, tetra-n-butyltitanate, tetrakis(2-ethylhexyl)titanate and diisopropyldiisostearyltitanate.

14. A composition as claimed in claim 10, wherein the bonding agent is a titanate chelate compound of the formula:

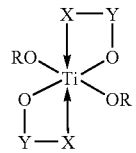

wherein
each R independently represents a straight or branched $C_{2-20}$ alkyl group.
X represents a functional group containing oxygen or nitrogen, and
Y represents a two or three carbon chain.

15. A composition as claimed in claim 10, wherein the bonding agent is selected from the group consisting of acetylacetonate titanate chelate, ethyl acetoacetate titanate chelate, triethanolamine titanate chelate, and lactic acid titanate chelate (ammonium salt).

16. A composition as claimed in claim 10, wherein the bonding agent is an organozirconate compound of the formula:

wherein each R independently represents a straight or branched $C_{2-20}$ alkyl group.

17. A composition as claimed in claim 10, wherein the bonding agent is selected from the group consisting of zirconium tetra-n-butanolate and zirconium tetra-n-propanolate.

18. A composition as claimed in claim 10, wherein the bonding agent is an organosilicate compound of the formula:

wherein each R independently represents a straight or branched chain $C_{2-20}$ alkyl group.

19. A composition as claimed in claim 10, wherein the bonding agent is tetraethylorthosilicate.

20. A composition as claimed in claim 10, which comprises from about 0.001% to about 25%, by weight of the composition, of the bonding agent.

21. A composition as claimed in claim 10, which is formulated as an emulsion, including oil-in-water, water-in-oil, water-in-oil-in-water, oil-in-water-in-oil, water-in-silicone and oil-in-water-in-silicone emulsions.

22. A method of conferring a cosmetic and/or therapeutic benefit upon a person, which method comprises applying a composition as claimed in claim 10 to the skin, hair, nails, lips or mucous membranes of that person.

23. A method for improving the substantivity of a benefit agent, which method involves the application to a substrate of separate compositions, one of which contains a bonding agent having hydrolysable or exchangeable ligands selected from the group consisting of organotitanates, organozirconates and organosilicates, which will act to covalently link the benefit agent to a substrate to which the compositions are applied, and the other of which contains the benefit agent, wherein the separate compositions become mixed on the substrate.

* * * * *